US012209235B2

(12) United States Patent
Gebauer et al.

(10) Patent No.: US 12,209,235 B2
(45) Date of Patent: Jan. 28, 2025

(54) DETECTION OF FOAM LEVELS

(71) Applicant: CYTIVA SWEDEN AB, Uppsala (SE)

(72) Inventors: Klaus Gebauer, Uppsala (SE); Pierre Le Greves, Uppsala (SE); Andrew David Pris, Niskayuna, NY (US); Jozsef Vasi, Uppsala (SE); Sam Petrocelli, Old Tappan, NJ (US); Hanno Ehring, Uppsala (SE); Esmaeil Heidari, Niskayuna, NY (US); Ali Can, Niskayuna, NY (US)

(73) Assignee: CYTIVA SWEDEN AB, Uppsala (SE)

( * ) Notice: Subject to any disclaimer, the term of this patent is extended or adjusted under 35 U.S.C. 154(b) by 1485 days.

(21) Appl. No.: 16/328,431

(22) PCT Filed: Aug. 28, 2017

(86) PCT No.: PCT/US2017/048793
§ 371 (c)(1),
(2) Date: Feb. 26, 2019

(87) PCT Pub. No.: WO2018/044748
PCT Pub. Date: Mar. 8, 2018

(65) Prior Publication Data
US 2021/0123010 A1     Apr. 29, 2021

(30) Foreign Application Priority Data
Aug. 31, 2016 (GB) ..................... 1614717

(51) Int. Cl.
*C12M 1/21* (2006.01)
*C12M 1/00* (2006.01)
*C12M 1/36* (2006.01)

(52) U.S. Cl.
CPC ............ *C12M 41/02* (2013.01); *C12M 23/14* (2013.01); *C12M 23/22* (2013.01); *C12M 31/02* (2013.01);
(Continued)

(58) Field of Classification Search
CPC ...... C12M 41/02; C12M 23/14; C12M 23/22; C12M 31/02; C12M 31/10; C12M 41/06; C12M 41/48
See application file for complete search history.

(56) References Cited

U.S. PATENT DOCUMENTS 3,739,795 A * 6/1973 Hyde ..................... G05D 21/02
137/5
4,247,784 A * 1/1981 Henry .................. G01F 23/2928
250/577
(Continued)

FOREIGN PATENT DOCUMENTS

AT          260289      12/1993
CN        101509801      8/2009
(Continued)

OTHER PUBLICATIONS

Database WPI; Week 201415, Thomas Scientific, London GB; An 2014-D66163; XP002775634; Shanghai Likong Machinery & Electronics; Dec. 25, 2013.
(Continued)

*Primary Examiner* — Tarun Sinha
(74) *Attorney, Agent, or Firm* — Grogan, Tuccillo & Vanderleeden, LLP

(57) ABSTRACT

A device and method for detecting the level of foam in a reactor vessel monitors the intensity of the light or the movement of the light detected by a camera which monitors at least one light source positioned inside the reactor vessel or viewable through the reactor vessel.

21 Claims, 18 Drawing Sheets

(52) U.S. Cl.
CPC ............ *C12M 31/10* (2013.01); *C12M 41/06* (2013.01); *C12M 41/48* (2013.01)

(56) References Cited

U.S. PATENT DOCUMENTS

| | | | |
|---|---|---|---|
| 4,952,509 | A | 8/1990 | Wagner et al. |
| 5,108,655 | A | 4/1992 | Johns, Jr. et al. |
| 5,542,004 | A | 7/1996 | Constant et al. |
| 5,597,950 | A * | 1/1997 | Mullen .................. G01N 27/06 73/866 |
| 6,782,122 | B1 * | 8/2004 | Kline .................. G01F 23/292 382/142 |
| 2002/0088823 | A1 | 7/2002 | Tabacchi et al. |
| 2004/0083892 | A1 | 5/2004 | Simon, Jr. et al. |
| 2004/0142481 | A1 | 7/2004 | Hartlein |
| 2011/0268329 | A1 * | 11/2011 | Pronkine .................. G01F 23/804 382/128 |
| 2013/0039810 | A1 * | 2/2013 | Riechers .................. C12M 41/02 422/82.05 |
| 2016/0046899 | A1 | 2/2016 | Garnier et al. |

FOREIGN PATENT DOCUMENTS

| | | |
|---|---|---|
| CN | 102519540 | 6/2012 |
| CN | 103278509 | 9/2013 |
| CN | 103314293 | 9/2013 |
| CN | 103472069 A | 12/2013 |
| CN | 204162717 | 2/2015 |
| DE | 20011718 | 11/2000 |
| DE | 102010007559 A1 | 8/2011 |
| DE | 102010012162 A1 | 9/2011 |
| DE | 102010045409 A1 | 3/2012 |
| EP | 2150609 A1 | 2/2010 |
| EP | 2371942 A2 | 10/2011 |
| JP | 2009080072 A | 4/2009 |
| JP | 2010220499 A | 10/2010 |

OTHER PUBLICATIONS

Database WPI; Week 200928; Thomas Scientific, London GB; AN 2009-H09473; XP002775428; Matsushita Denki Sangyo KK) Apr. 16, 2009.

Database WPI; Week 201068, Thomas Scientific, London GB; AN 2010-M71811; XP002775429; Meiji Milk Prod. Co. Ltd.; Oct. 7, 2010.

International Search Report and Written Opinion from corresponding PCT Patent Application No. PCT/US2017/048793 dated Nov. 24, 2017.

Combined Search and Examination Report from corresponding GB Patent Application No. 1614717.5 dated Dec. 13, 2016.

English Translation of Office Action issued in corresponding Chinese Application No. 201780052916.3 dated Jul. 12, 2022.

Office Action issued in corresponding CN Application No. 201780052916.3 dated Nov. 29, 2021.

* cited by examiner

DETECTION OF FOAM LEVELS

CROSS REFERENCE TO RELATED APPLICATION

This application is a national stage application of International Application No. PCT/US2017/048793 filed on Aug. 28, 2017 which claims priority to United Kingdom Patent Application No. 1614717.5 filed on Aug. 31, 2016, which are hereby incorporated in their entireties.

BACKGROUND OF THE INVENTION

A bioreactor is a device or system that supports a biologically active environment. One type of a bioreactor is a single use, disposable reactor bag or other vessel in which a biological or chemical process is carried out which involves cells, organisms or biochemically active substances derived from such cells or organisms. A typical example of a bioreactor is a vessel comprising a suspension of animal cells or microorganisms producing an antibody, a vaccine antigen or other type of biopharmaceutical. Foam occurs in bioprocesses due to, amongst others, the introduction of gases into the culture medium, and proteins and/or other components of the culture medium can contribute to the foaming. The foam may be further stabilized by proteins produced by organisms in the culture. Foaming can lead to reduced process productivity since bursting bubbles can damage proteins, result in loss of sterility if the foam escapes the bioreactor, or lead to over-pressure if a foam-out blocks an exit filter. To prevent the formation of foam, chemical antifoaming agents (or "antifoams", "de-foaming agents", "defoamers" etc., all used synonymously) are routinely employed in bioreactors. The use of antifoams however may not only destroy foam, but may also affect the cells (and the proteins produced by them) in the reactor. For example, the foam may negatively affect gas transfer from air to liquid resulting in an undesirably reduced dissolved oxygen level in the culture. It is therefore desirable to regulate the use of antifoams so that an optimum amount of antifoam is used—for example enough to prevent the blocking of outlets while minimizing the effect the antifoam has on the biological process taking place in the bioreactor. In order to do this, it is necessary to monitor the amount of foam in the bioreactor and to only add antifoam when the monitoring reveals that the amount of foam exceeds a predetermined safe level. This may be done manually but requires continuous monitoring and a risk of operator error that makes manual system undesirable.

Detecting foam during bioreactions such as fermentation or cell culturing in reactor vessels such as bags can be achieved by inserting radar or ultrasonic probes inside the bag but this is undesirable as there is a risk of contamination of the contents of the bag or fouling of the probes by foam residues and an increased risk of leaks. Detecting the level of foam without inserting probes inside the bag is a challenge.

BRIEF DESCRIPTION OF THE INVENTION

The present invention overcomes some of the problems with the prior art by providing an automated system for detecting and controlling the level of foam in a reactor vessel. The reactor vessel may have at least one column or array of vertically separated light sources provided on a vertically-extending wall. Bioreactor support vessels which are intended for supporting disposable, single-use process bags usually have an open top and at least one camera or light detector for detecting any light from the light sources that passes through the bag can be mounted at or near the top of the support vessel opposite or obliquely opposite the light sources. Alternatively, in closed vessels, the wall opposite the light sources can be made translucent or transparent or provided with a transparent or translucent window through which the light from the light sources can be detected by a camera mounted on the outside of the wall or window. When the bioreactor vessel or bag is loaded with a bioculture the lights that are at levels which are below the level of the surface of the bioculture will be obscured by the bioculture while those that are above the surface of the bioculture will be visible. Preferably prior to the commencement of a bio-reaction a calibration of the number and/or intensity of visible lights is performed by software. During the bioprocess foam will be formed and form a layer on top of the bioculture. The colour and intensity of the light sources is chosen such that the intensity of the light from a light source detected by the camera is significantly changed (reduced or increased depending on the optical arrangement, as further discussed below) when the level of the foam is above the level of the light source or approaches the level of the light source. The camera monitors the light sources and the number of visible lights and/or the intensity of the visible lights is compared against the original number and/or intensity of lights and, in the absence of fluid being added or removed from the reactor vessel, any change in the number of visible lights and/or their intensities will be assumed to be due to the presence of foam. The system is provided with a source of antifoaming agent and means such as software-controlled pump and/or valves for performing the addition of the antifoaming agent to the reactor vessel. The addition of antifoam may thereafter be regulated by the software in accordance with changes in the number of lights or light intensity detected by the camera—for example if a predetermined change in the number of visible lights or their intensities is detected then the software will trigger the addition of antifoam. Preferably, the camera picture can be shown on the control screen in order to give an operator a view of the culture in real time.

The invention further discloses an automated active light computer vision system for monitoring foam thickness and height in bioreactors. The system is also able to measure the rate of change of foam thickness and height. The system comprises an actively controlled light source, and a light detector or camera system collecting scattered and reflected light from the foam inside a bioreactor. In some embodiments, two LED light columns are installed inside a bioreactor support vessel (between the bag and the vessel) without any major modifications to the vessel, and a camera can be placed at the top of the bioreactor to collect scattered photons. When the two LED columns are placed on a planar geometry, it is easy to estimate the 3D to 2D perspective projection parameters from a plane in 3D to a plane in camera coordinate system, hence calculate photon counts accurately in regions of interest defined in real 3D coordinate systems. Several other optical systems are also described as further embodiments.

Yet further, the invention discloses a closed loop automated de-foaming system. This de-foaming system comprises a foam thickness measurement system, a control system and a pump system. The control box that controls the pump to dispense appropriate amount of de-foaming agent is based on information it receives from the thickness measurement system. The foam thickness measurement system comprises LED lights or other light sources that scatter photons forward and backward in the foam regions. The measurement also comprises a light detector or photon counting device such as a CCD or CMOS camera that captures scattered light from the foam region, or reflected light from the top of the foam. The light sources are suitably placed between a bioreactor bag and a bioreactor support vessel. The foam thickness measurement system measures the foam thickness and communicates with the pump control. When the foam thickness goes above a certain threshold, the control system sends a signal to turn on the de-foaming agent pump valve to dispense an appropriate volume in the bioreactor tank/bag. The foam thickness decreases as the de-foaming agent dosage completely releases in the cell culture media. The invention also accurately predicts and delivers how much de-foaming agent is required to lower the foam thickness in a desired time interval. Since the system prevents overusing defoaming agents, it is superior to manual systems where amount of defoaming agent is guessed by an operator. The disclosed system also increases the quality of the cell culture and cell viability due to decreased side-effects of defoaming agents.

This system includes foam thickness measurement system, the de-foaming pump and controller. In this closed loop system when the foam becomes thick enough, the de-foaming agent will be dispensed and the system will be able to measure the de-foaming rate simultaneously.

Figure 15:
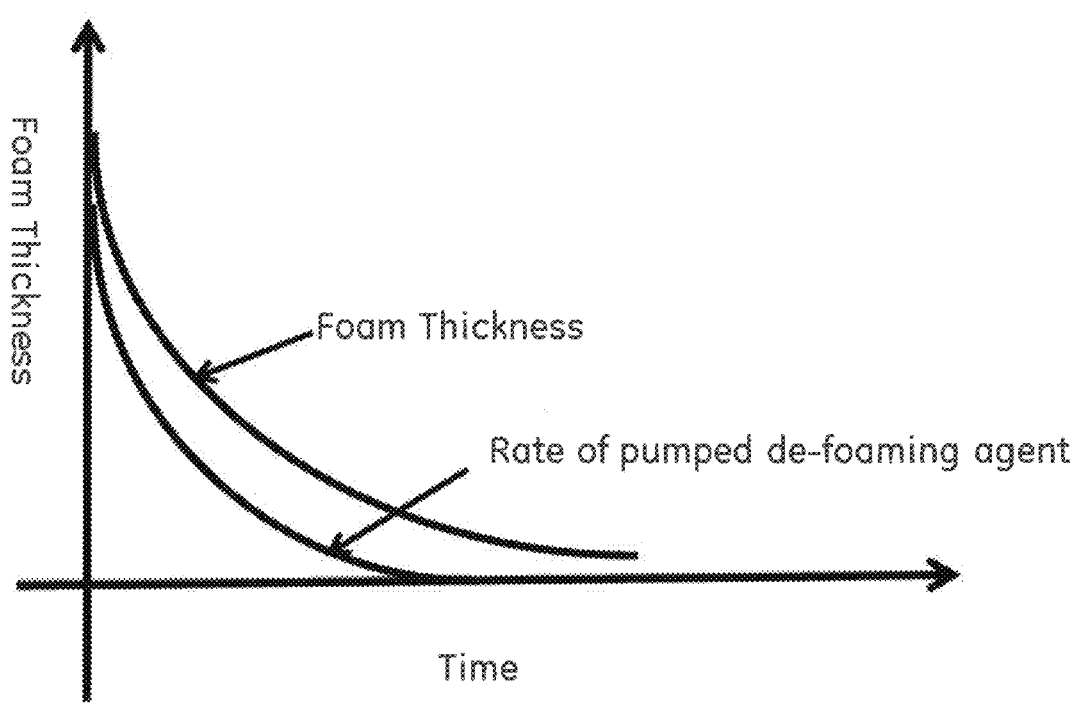

FIG. 15 shows how the rate of foam thickness decreases as the de-foaming agent dosage completely releases in the cell culture media.

Figure 16:
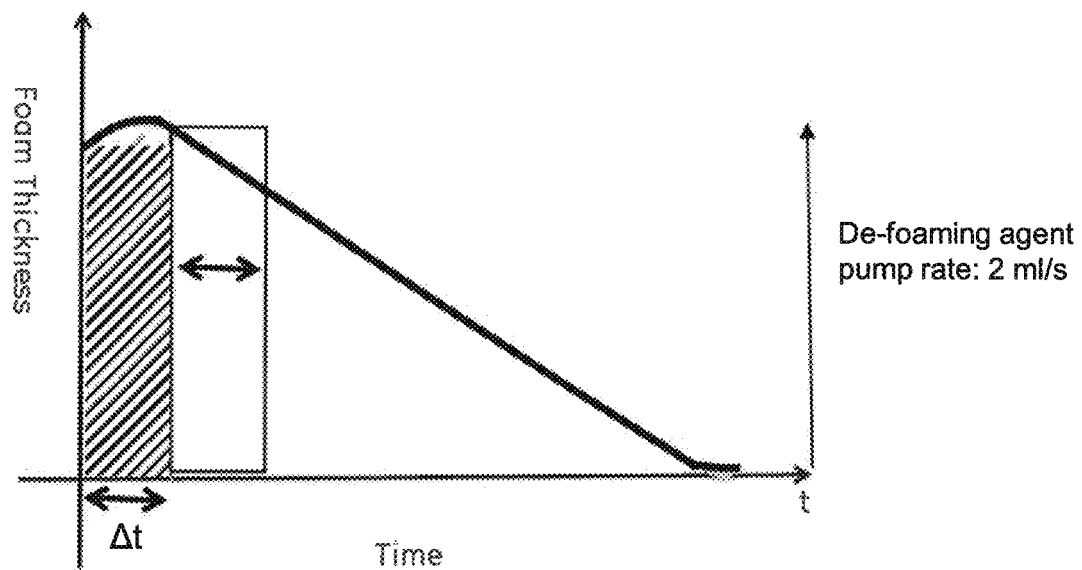

FIG. 16 shows the de-foaming rate correlation with foam thickness in a closed loop de-foaming system.

Figure 17:
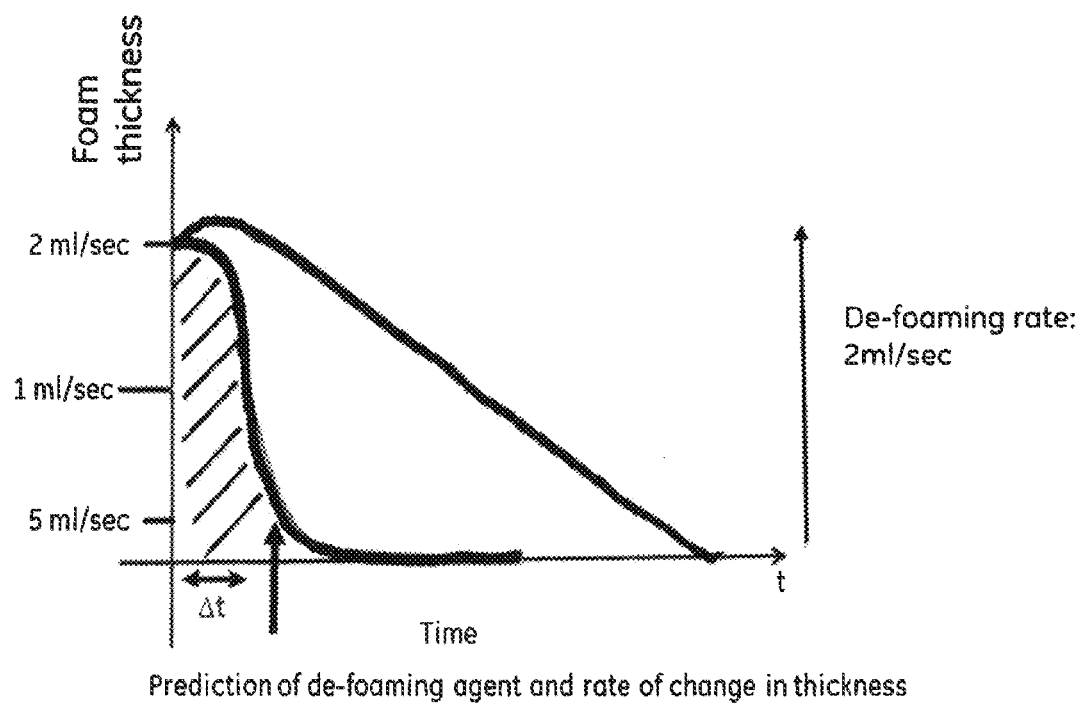

FIG. 17 shows how the operator can predict accurately how much de-foaming agent is required for lowering the foam thickness at a desired time.

Definitions a) To more clearly and concisely describe and point out the subject matter of the claimed invention, the following definitions are provided for specific terms that are used in the following description and the claims appended hereto.

b) The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified.

c) Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

d) As used herein to describe the present invention, directional terms such as "up", down", "top", "bottom", "vertical", "horizontal", as well as any other directional terms, refer to the directions as shown in the appended drawings. Those are also the directions of a reactor vessel or bioreactor as used in the normal operational position.

The term "column" herein means a vertically spaced assembly of objects, such as light sources or light detectors/cameras. The column may e.g. be in the form of a vertical line or a staggered or oblique line. The column can suitably have one single object/light source/detector in each vertical position.

The term "array" herein means a vertically and horizontally spaced assembly of objects, such as light sources or light detectors/cameras. The array may e.g. comprise a plurality of columns. It may also be described as comprising a plurality of vertically spaced rows, where each row comprises a plurality of horizontally spaced objects/light sources, e.g. in the form of a horizontal line or a staggered or oblique line. A row may suitably have one single object/light source/detector in each horizontal position.

DETAILED DESCRIPTION OF THE INVENTION

Figure 1:
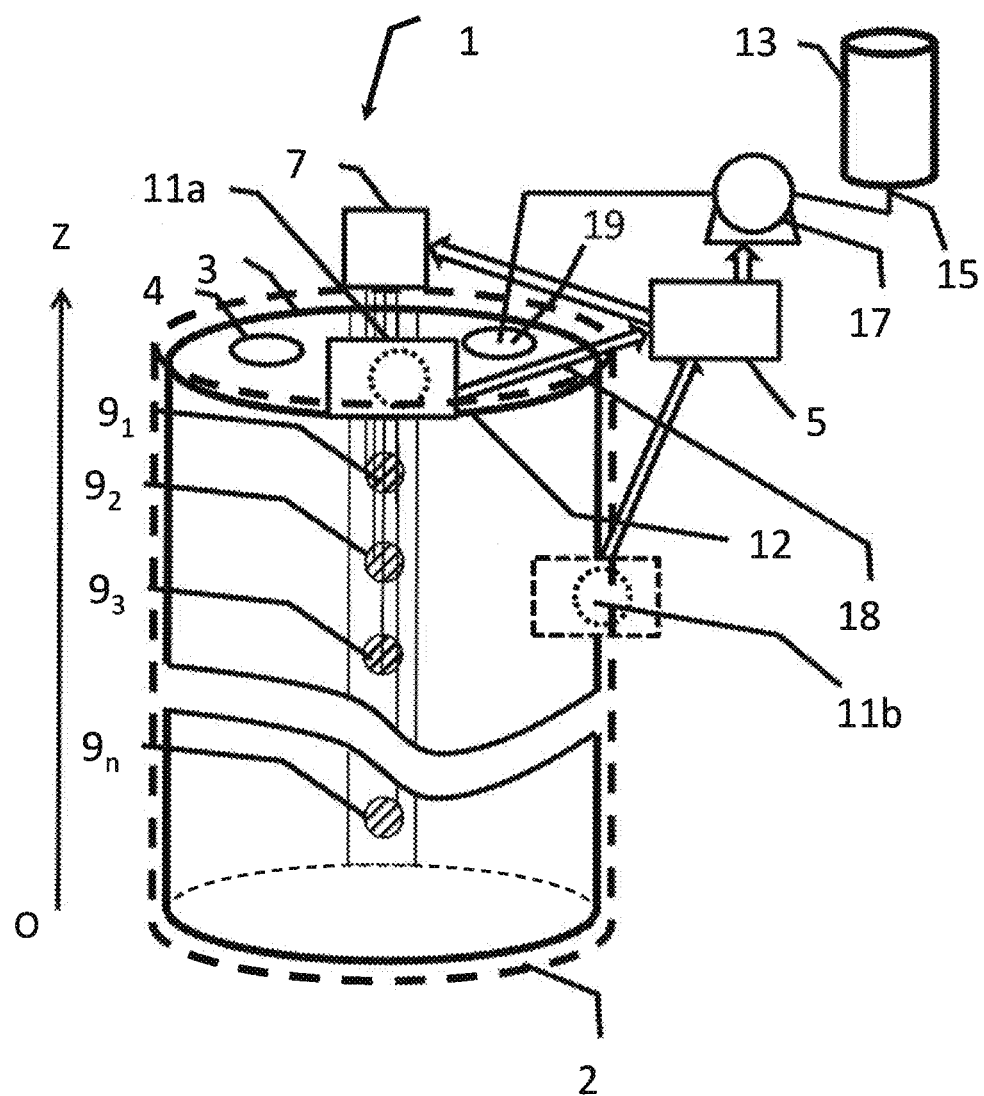
FIG. 1 shows schematically a system for controlling foaming in a reactor vessel in accordance with a first embodiment of the invention.

A system for controlling foaming in a bioreactor system using single-use bags is shown schematically in FIG. 1. The system 1 comprises a mantled rigid (e.g. stainless steel) open reactor vessel 2 (shown by dashed lines) adapted to support and maintain at the correct temperature an airtight single use transparent plastic reactor bag 3. The bioculture which is necessary for a bioprocess can be loaded into the bag via an inlet port 4 on the bag. In order to control foaming, a control device 5 such as a microprocessor or computer is connected to a power supply 7 which provides power to a series of light sources $9_1$ to $9_n$ which are provided on or near to a side wall of the reactor vessel. These light sources are arranged at different heights from the base of the reactor vessel e.g. in the form of a vertical line or a staggered or oblique line. Alternatively, a light source extending in a vertical direction can also be used, e.g. a vertical or oblique fluorescent tube. In this case, different segments of the light source can be treated as the individual light sources discussed above. Control device 5 is connected to at least one camera 11a which is attached to the upper edge 12 of the reactor vessel wall and is aimed towards the column of lights from the opposite side of the reactor vessel such that any light emitted by the light sources must pass through the transparent bag 3 before being received by the camera. If the reactor vessel has transparent walls or windows then the camera may be placed elsewhere opposite the light sources such that light from the light sources must pass through the transparent bag 3 before being received by the camera, for example in front of the side of the reactor vessel obliquely opposite the light sources as shown by camera 11b (shown by dashed lines). Having the camera near the top end of the vessel has the advantage that the light only has to travel a relatively short distance through the foam layer and then through a top wall of the bag, which may be less contaminated with cells and foam residues than the side walls. Control device 5 is connected to a pump 17 which controls the flow of an antifoam agent from the outlet port 15 of an antifoam-containing reservoir 13 to an inlet port 19 in the top 18 of the bag.

Figure 2:
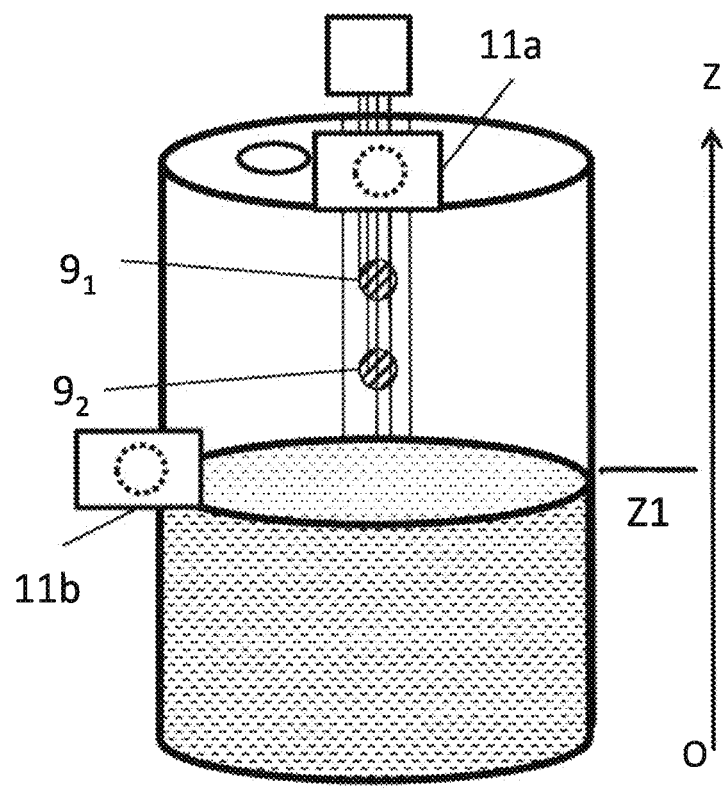
FIG. 2 shows schematically the reactor bag of FIG. 1 containing a volume of bioculture.
Figure 3:
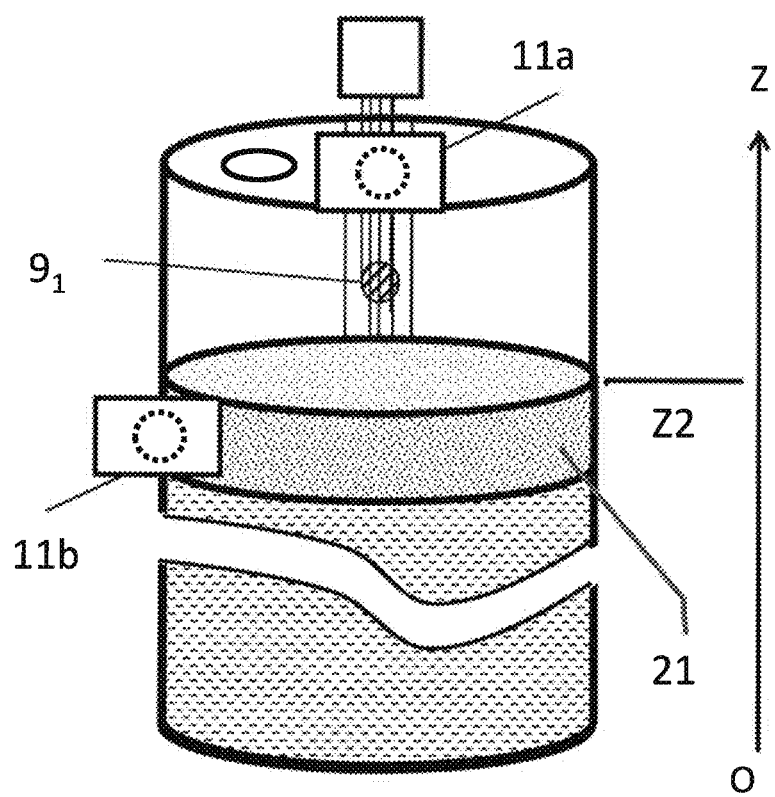
FIG. 3 shows schematically the reactor bag of FIG. 2 wherein the bioculture has been covered with a layer of foam.
Figure 4:
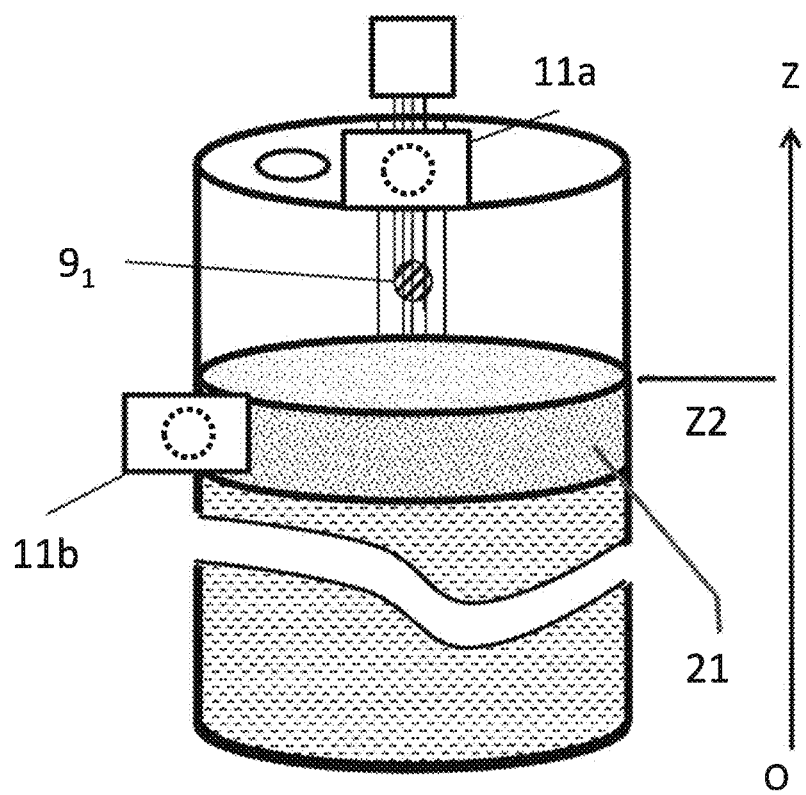
FIG. 4 shows schematically the reactor bag of FIG. 3 after the thickness of the layer of foam has increased.
Figure 5:
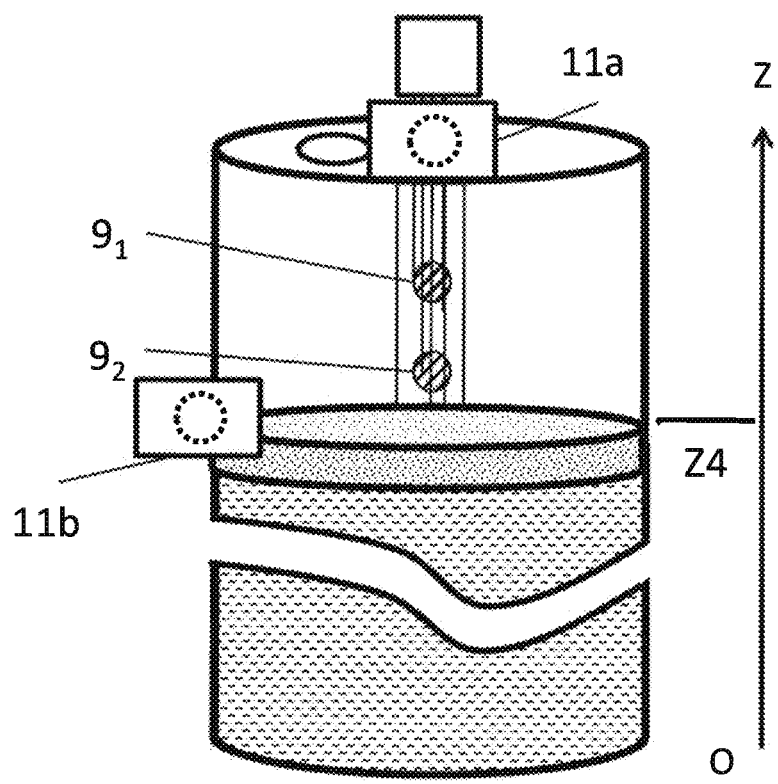
FIG. 5 shows schematically the reactor bag of FIG. 4 following the application of antifoam agent.

In order to improve clarity of illustration, FIGS. 2 to 5 only show the details of the reactor bag and light sources necessary to comprehend the invention. FIG. 2 shows the bag of FIG. 1 after the bioreactor bag has been partially filled with the bioculture needed for the intended cultivation. The bioculture is cloudy or opaque so that the light emitted from the lights sources $9_3$ to $9_n$ below the level of bioculture is prevented from being detected by the camera.

The foam scatters and reflects light in such a way that when the camera is in position 11b (on the side wall), a light source $9_n$ immersed in the foam 21 (FIGS. 3-5) will be essentially invisible to the camera 11b, as the light will have to travel the entire diameter of the vessel through the foam and the contrast will be lost primarily due to multiple scattering.

When the camera is in position 11a (by the top of the vessel), the situation is different: A light source $9_n$ far above the foam 21 will be highly visible as a small bright dot against a black background, although with a relatively low total photon count, as the camera 11a only captures the portion of light going in the direction of the camera (the light source emits photons in all directions). When the light source is closer to the top of the foam, the camera will also capture diffusely reflected light from the foam (thus capturing light from wider angles), leading to an increase in photon count as the distance between the light source and the foam decreases. When the light source is immersed in the foam near the top, the photon count will still be high due to forward light scattering in the foam, but as the immersion depth increases, the photon count will decrease due to multiple scattering effects. When the light source is immersed in the opaque liquid below the foam, the photon count will be essentially zero. These effects are also illustrated by the experimental results of FIG. 12.

The control device is preferably provided with software able to run an antifoam program. The antifoam program may comprise the following steps when the camera is in position 11b: When the program is initiated the program runs a calibration subroutine which detects the starting level of the bioculture e.g. height $Z_1$ shown in FIG. 2. In this subroutine the program processes the image from the camera and records which of the light sources arranged on the reactor vessel are visible to the camera in order to determine the starting level of the bioculture or other liquid in the reactor vessel. For example, if only light sources $9_1$ and $9_2$ are visible then the starting level is between the heights of light sources $9_2$ (which is visible) and $9_3$ (which is not visible). Of course, the starting level is dependent on factors such as the temperature of the liquid in the bioreactor and the rate of aeration provided to the liquid. In order to minimize the effect of changes in the level of liquid caused by temperate changes and aeration, the calibration is preferably performed as soon as the liquid have achieved the correct reaction temperature and the aeration has been set at the starting level. In the event that aeration levels are liable to change during the process the calibration can be performed at different aeration rates in order to provide the data necessary to compensate for changes in the level of the liquid caused by increased entrapment of gas bubbles due to increased aeration rates.

Once the starting level of the bioculture or liquid has been determined and any measurements necessary to compensate for different aeration rates performed, the control device checks the image from the camera at predetermined time intervals. If foaming occurs (as shown by layer 21 in FIG. 3) it will start to cover the light source $9_2$, thus reducing the intensity of the light detected by the camera 11b. If the layer of foam is deep enough it will completely prevent light from light source $9_2$ from being detected by the camera—thus it has reached the height $Z_2$ shown in FIG. 3. At this point the control device determines that the thickness of the layer of foam is the same as the distance between the original height of the liquid and the distance between that height and the top of light source $9_2$. If this thickness of foam is acceptable then the control unit continues to monitor the level of foam but does not take any further action. However, if the amount of light detected by the camera from the higher light source $9_1$ begins to fall then this could be a sign that the level of foam is increasing. If the amount of light from light source $9_1$ detected by the camera falls below a predetermined intensity, for example 50% of the original value or 0% of the original value (i.e. no light at all is detected—which corresponds to the foam reaching the height $Z_3$ shown in FIG. 4) then control unit 13 activates pump 17 to add a predetermined quantity of antifoam agent from reservoir 13 via outlet 15 to the inlet 19 of the bag (FIG. 1). This antifoam agent reduces the level of foam thus allowing more light from light source $9_1$ to be detected by the camera as shown by level $Z_4$ in FIG. 5. The control device continues to monitor the output from the camera and if the level of light detected from light source $9_1$ does not return to its previous intensity within a predetermined time interval then the control unit may determine that it is necessary to apply a further quantity of antifoam agent to the bag as this lower light intensity may be due to the continued presence of a high level of foam. However, it is possible that the lack of intensity is not due to a high level of foam in the bag but merely due to residual foam clinging to the walls of the reactor bag, thus diminishing the intensity of the light from light source $9_1$ passing through the bag. In order to prevent an unnecessary injection of antifoam agent, the control device can be provided with an algorithm for determining whether the injection of further antifoam agent is necessary if the situation occurs that the light detected from a previously obscured light source does not return to its original value. For example, the algorithm may determine that if after the predetermined time interval the light detected from a previously obscured light source is equal to or greater than 50% of its original value then no further antifoam agent is injected—the reduced amount of light being assumed to be due to contamination of the bag wall by residual foam. With the camera in position 11a, a similar antifoam program may be used, taking into account that the photon count for the light sources above the liquid level increases as foam starts to form and decreases when antifoam is pumped in and starts to act on the foam.

The program continues to monitor the data from the camera regarding the visibility of light sources and the amount of light detected from them, and applies antifoam agent as necessary.

If further bioculture or other substances are added to the bioculture in the bag, then the change in volume will cause the surface of the bioculture to move up towards the top of the vessel. This may obscure one or more of the light sources and may be misidentified as being a layer of foam. This might initiate the pumping of antifoam agent into the reactor vessel—even if this is unnecessary. In order to prevent this, the weight of the reactor vessel can be detected by load cells and any change in weight can be converted in the software into a theoretical change in the liquid level. The starting liquid level can then be recalculated by adding theoretical changes in the liquid level to the starting level. This if the original starting level was $Z_1$ and the amount of liquid added to the reactor vessel is calculated to cause a rise of A cm in the liquid level, then after the addition of the liquid the software replaces the original starting level of $Z_1$ with a new theoretical starting level which is the sum of $Z_1$ and A in future calculations. Alternatively, or additionally, the software may be provided with a recalibration subroutine. This may be in the form of a subroutine which can be initiated by an operator, or automatically by control means when it detects the addition of bioculture to the reactor vessel (for example by monitoring the opening and closing of an inlet valve of the reactor vessel or by monitoring the weight of the reactor vessel). The subroutine follows the original calibration subroutine and thus determines which of the light sources are visible after addition of the extra substances. The level of the lowest visible light source now becomes the starting level $Z_0$ used in further iterations of the program.

Figure 6:
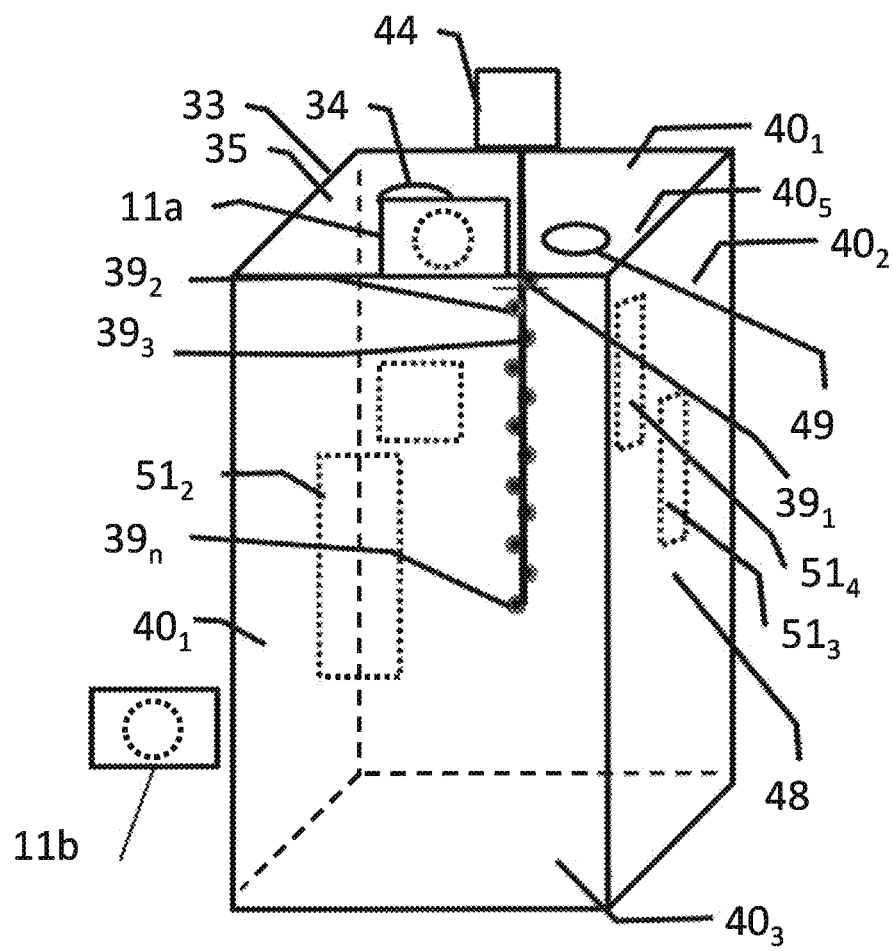
FIG. 6 shows schematically a reactor vessel in accordance with a further embodiment of the invention.

FIG. 6 shows a further embodiment of a reactor vessel 33 according to the invention. Reactor vessel 33 is a container made of stainless steel, glass or plastic adapted to maintain at the correct temperature a bioculture. In this example the vessel is cubic but it may of course be cylindrical, hemispherical or any other shape. The vessel has a rear wall $40_1$, a first side wall $40_2$, a front wall $40_3$, a second side wall $40_4$, an upper face $40_5$ and a lower face $40_6$. The upper face of the vessel comprises upper inlet ports 34 and 49 for the introduction of liquids and anti-foaming agent, respectively. A series of vertically spaced light sources for example LEDs $39_1$ to $39_n$ are provided on the wall $40_1$ of the vessel 33 with light source $39_1$ nearest to the top of the vessel and light source $39_n$ nearest the bottom of the vessel. The vessel is adapted so that the light sources can be detected by a camera 11a, 11b (see above for the differences in data handling for the 11a and 11b positions). In open reactor support vessels for transparent plastic bag bioreactors or reactor vessels with a transparent upper face $40_5$ the camera 11a can be mounted on the upper edge of the reactor vessel or reactor support vessel wall. In the case of closed vessels, a window (see in the vessel is positioned opposite to the light sources (see for example windows $51_1$, $51_2$), or obliquely to the light sources on a side wall (see for example windows $51_3$, $51_4$ on side wall $50_2$) such that light from each light source must pass though the interior by the bag before reaching the window and hence to a camera 11*b* mounted outside the vessel. This ensures that the light from a light source will be obscured from view from the window if the level of the liquid inside the bag is higher than the level of that light source. Depending on the transparency of the vessel walls these light sources may be attached to the outside of the wall (if the wall is transparent or provided with a window there) or to the inside of the wall (if a camera is arranged to look into the vessel from above or if the walls between the camera and light source are adapted to let light pass through them). The light sources are connected to a terminal block or plug 44 or other means for providing them with electrical power. Foaming in the vessel can be controlled by means of a program and method as described above.

While the detection of a level of foam can be achieved with only two vertically spaced light sources, in all embodiments of the invention the number of light sources is preferably equal to or greater than 3 in order to allow more precision in detecting the presence of foam and to allow redundancy in the case of the failure of one light source. More preferably the number of lights sources is greater than or equal to ten and most preferably the number of light sources is equal to or greater than 20. Furthermore, each embodiment of the invention can be provided with two or more independently energized and controlled sets of vertically spaced light sources to provide redundancy in the case of the failure of one set of light sources.

In the above described embodiments of the invention the light sources may be arranged inside the reactor vessel or they may be arranged outside the reactor vessel on the exterior surface of a window or transparent wall or on a frame provided near or attached to the reactor. In the case of a transparent plastic bag bioreactor in a rigid bioreactor support vessel, the light sources can be arranged between the bag and an inner wall of the support vessel, if so desired in a recess on the inner wall. The light sources may be any type of electromagnetic radiation emitting or reflecting device such as LEDs, incandescent light bulbs or the like. In particular, the light sources can emit visible light. Small, low cost individually addressable light sources of high reliability, such as LEDs that can easily be assembled into strips or sheets to be mounted as columns or arrays are particularly useful. Alternatively, the light sources may be reflective patches or areas or (retro)reflectors that are illuminated by one or more lamps or the like. The lamp(s) could be adjacent to the camera or provided elsewhere. The light may be visible light or it may be near infrared so that it is not visible. However, the shorter the wavelength then the higher the stray light formation will be, thus red or near infrared wavelengths are preferred. It is also possible to use light sources of different wavelengths to gather information about the foam morphology (e.g. density, bubble size and/or presence of particulates) from the wavelength dependency. Information about foam morphology may also be extracted from light intensity vs scattering angle data, e.g. by determining the spatial light intensity distribution over an image of a light source as captured with a camera through a foam layer or by performing other types of intensity vs. spatial distribution measurements. Preferably the distance between individual light sources in columns is 0.1 cm to 10 cm, such as 0.5-5 cm. An advantage of having several light source columns is that any errors from local foam residue deposits on the walls may be minimized or eliminated. For this purpose, it can be advantageous to have several light source columns with significant horizontal spacing, e.g. over at least 10 cm, such as at least 20 cm or at least 50 cm. To avoid saturating the camera the power of the light source should not be too high and will in the case of LEDs preferably be in of the order of microwatts.

Figure 7:
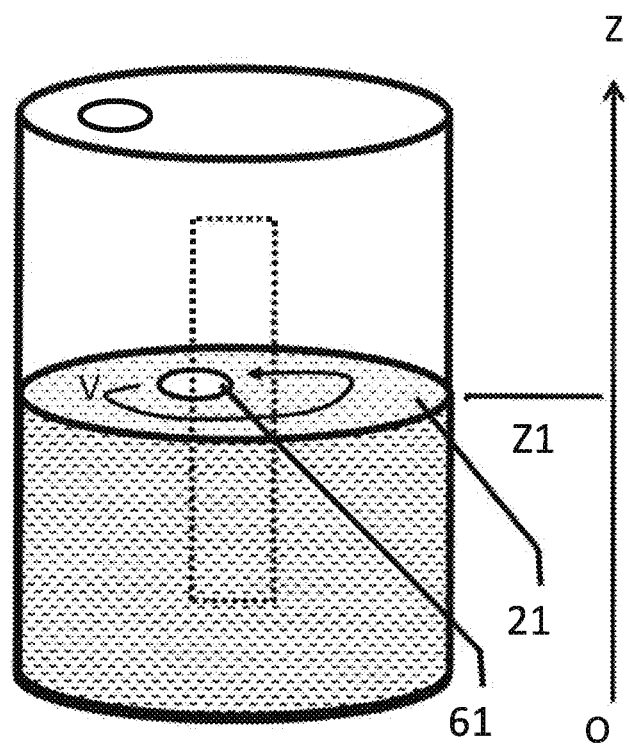
FIGS. 7 and 8 show details of a reactor vessel in accordance with another embodiment of the invention.
Figure 8:
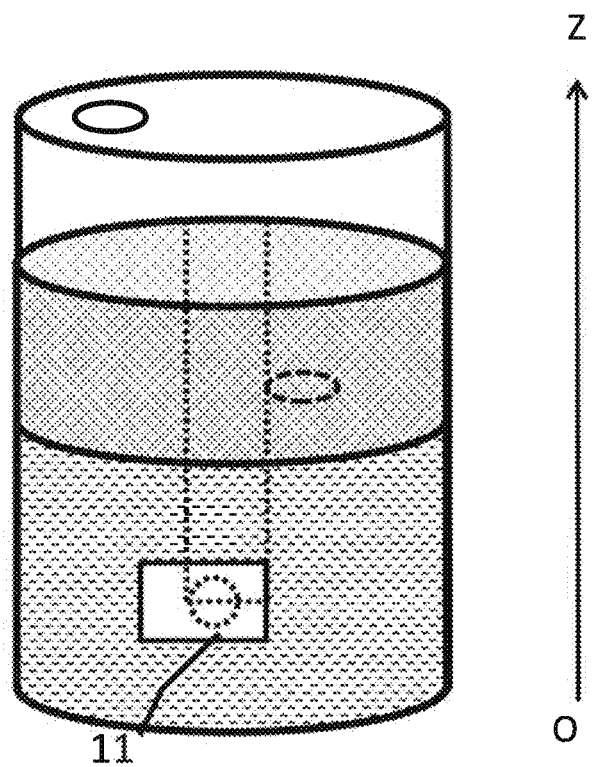

A further embodiment of the present invention is shown in FIGS. 7 and 8. This embodiment uses machine vision and image analysis for detecting the presence of foam on the surface of a liquid in a reactor vessel by tracking movement of a light source which is able to float on the surface. Suitably, the light source is capable of floating on the surface of an aqueous liquid having a density of about 0.95-1.2 g/l, such as a bioculture. Thus, a light reflecting or light-emitting floating object 61, which is suitably free to move on the liquid surface, is introduced into the reactor vessel and observed by a camera 11. As shown in in FIG. 7 when no foam is present, the liquid level is at $Z_1$ and the floating object quickly follows any changes in the level of the surface of the liquid and currents in the liquid causes it to move about on the surface, e.g. with a rotational movement if rotary agitation is used in the vessel. The velocity V (typically the lateral velocity induced by agitation of the liquid) of the floating object can be recorded at the beginning of the bioprocess and an average velocity or some other parameter representative of the movement of the floating object calculated. This can be done e.g. by recording the lateral position of the floating object vs time, dividing the distance traveled between two observations with the time interval between the observations to obtain a momentaneous velocity and averaging the momentaneous velocities over a predetermined time period. When foam is present as shown in FIG. 8, then the velocity of the floating object is reduced by friction caused by the foam so the parameter relating to velocity of the floating object would be reduced. A significant reduction in the parameter would then trigger the application of an antifoaming agent. Additionally, if the layer of foam is sufficiently thick such that the floating object is no longer visible (as shown by dotted lines in FIG. 8) then antifoaming agent could be applied in order to reverse the situation.

During operation of a bioreactor, the observations will be complicated by the presence of condensate and/or foam residues on the reactor walls in the headspace. Condensate droplets may act as lenses and deflect light, while foam residues will scatter and absorb light. These effects will in particular affect simple light absorption detectors where the intensity of light passing through the headspace from a light source to a detector is measured. Using a vertically spaced column or array of light sources and identifying visible and non-visible light sources as described above or detecting the movement velocity of a freely floating object (above) provides a foam detection system which is much more robust towards condensation and foam residue deposition in the bioreactor. It is also advantageous to use a camera adjacent to the top of the reactor vessel, as the amount of foam residues should be much lower than closer to the liquid level on the side wall. Further improvement of the robustness towards these factors can also be provided by the computer vision system for detection of scattered and reflected light from light source columns or arrays as discussed below.

Figure 9:
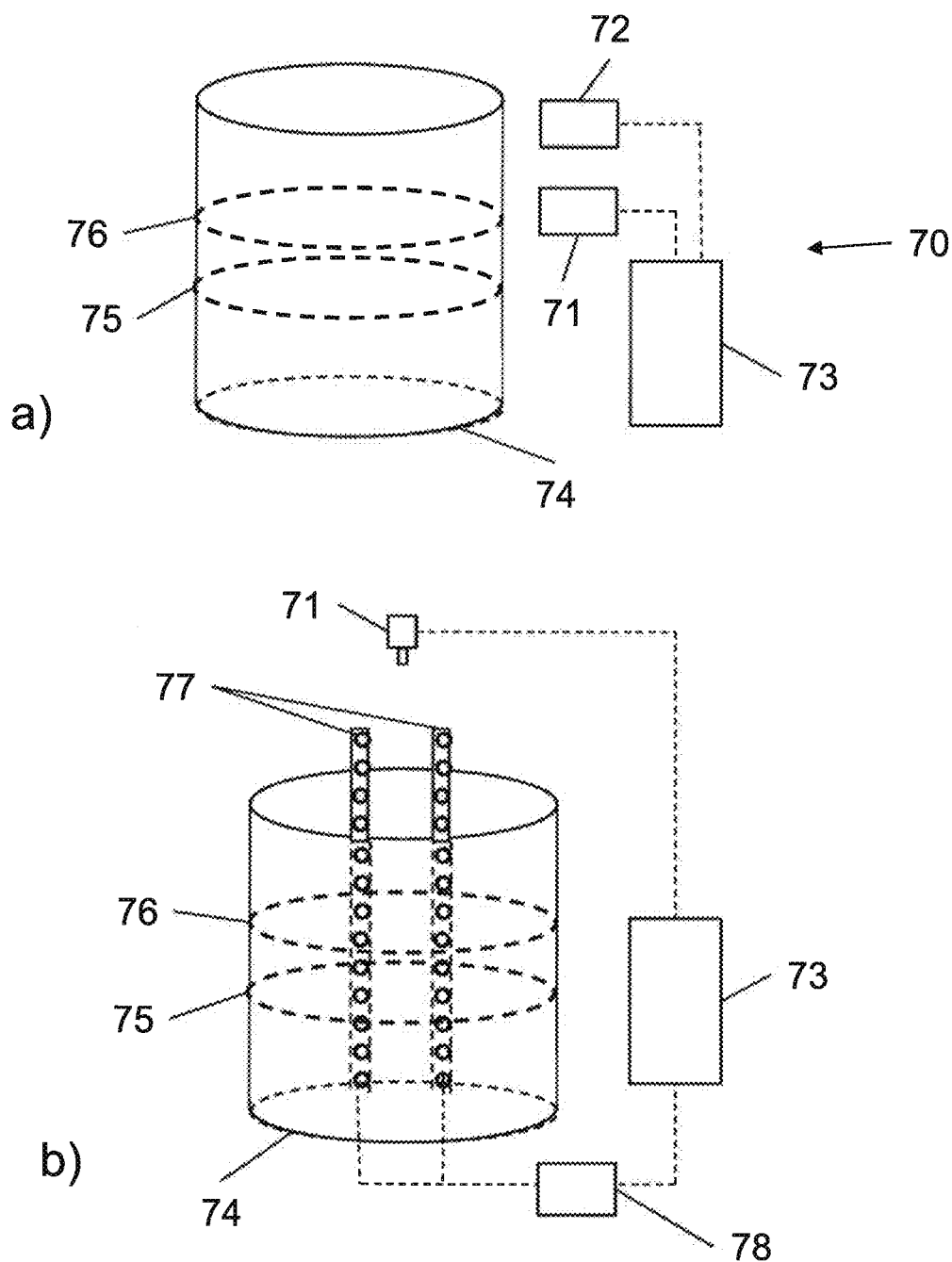
FIG. 9 shows:
a) An overview of an active light computer vision system comprising a camera that collects scattered and reflected light, an active light system, and a computer that controls the light system and the camera and processes data to measure foam thickness and foam height.
b) In some embodiments the camera system is positioned on the top of the bioreactor (where it can optically access the bioreactor), and the active light system comprises two LED columns where each LED light is triggered independently to collect a series of images at different heights. Two LED columns are used to calculate the perspective geometry from a set of homography formulations to easily compensate for image formation differences in the camera coordinate system. The second LED column can suitably be used only once during perspective geometry calibration, and then removed during monitoring, hence the monitoring can be done with only one LED column. Alternatively, under limited camera geometry configurations, a single column can also be used both for calibration and monitoring.

In this invention, as illustrated by FIG. 9*a*, we describe an active light computer vision system 70 that comprises a camera 71 that collects scattered and reflected light from an active light system 72, and a computer 73 that controls the light system and the camera and processes data to measure foam thickness and foam height in a reactor vessel 74 such as a bioreactor with a liquid level 75 and a foam level 76. In some embodiments, illustrated by FIG. 9*b,* the camera system 71 is positioned on or above the top of the bioreactor 74, and the active light system comprises at least one, such as at least two, light source (e.g. LED) columns 77 where each light source is triggered independently to collect a series of images at different heights. Two light source columns are used to calculate a perspective geometry from a set of homography formulations to easily compensate for image formation differences in the camera coordinate system. The second light source column can suitably be used only once during perspective geometry calibration, and then removed during monitoring, hence the monitoring can be done with only one light source column. Alternatively, under limited camera geometry configurations, a single column can also be used both for calibration and monitoring.

The system illustrated in FIG. 9b comprises a camera 71, two light source systems 77, a microcontroller/microprocessor 78 to trigger two addressable light source columns 77, and a computer 73 to send the address of the light source to the light source microcontroller. The computer collects images acquired by the camera. The computer is also used for all the calculations, such as estimating the perspective geometry parameters, and turning camera images to foam thickness measurements.

In the two light source column case, when these light source columns are placed such that they both lie on a plane geometry, a homography can be used to relate image coordinates to 3D world coordinates. Homography (also known as 3D perspective planar transform or collineation) is a well known projective planar transformation used in computational photography. See e.g. R Szeliski: Computer vision: Algorithms and Applications, Springer 2010, p. 36-37. A number of light source elements on both columns can be turned on one at a time and their coordinates in the camera coordinate system can be calculated, since their coordinates are also known in the 3D coordinate system, parameters of the following homography can be easily solved;

$$x' = \frac{h_{11}x + h_{12}y + h_{13}}{h_{31}x + h_{32}y + h_{33}}$$

$$y' = \frac{h_{21}x + h_{22}y + h_{23}}{h_{31}x + h_{32}y + h_{33}}$$

where (x',y') represents location of a light source element in camera coordinates, (x,y) represent light source locations defined in 3D world coordinates on an light source plane geometry (z=0), and $h_{i,j}$ (i,j=1,2,3) are the parameters of the homography. When two light source columns are placed on a plane geometry, the above equations are exact (not approximates), hence 4 points correspondences would be sufficient to solve them exactly. However, more points can be found with a least squares solution that minimizes the error in the light source locations, particularly the estimated locations on the camera coordinate system.

Figure 10:
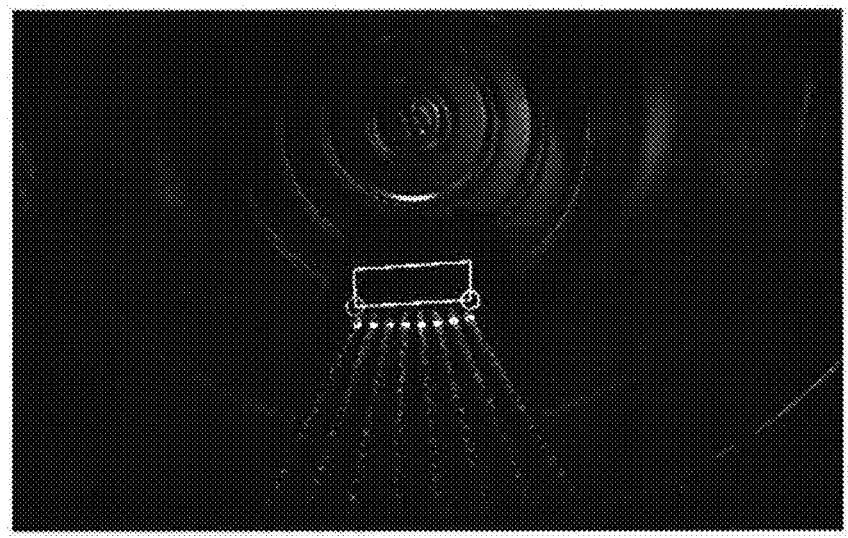
FIG. 10 shows an example configuration illustrating regions of interests (ROIs) for different LED heights. The rectangle in the top image shows an ROI at far field, and the bottom image is an example for near field. Since all LED elements reside on a plane in 3D real world coordinate system, a homography can be used to map 3D coordinates to camera coordinate system. Parameters of the homography transformation can be estimated by a set of point correspondences that are generated by individually turning on LED elements with known coordinates in 3D and in the camera coordinate system.
Figure 10:
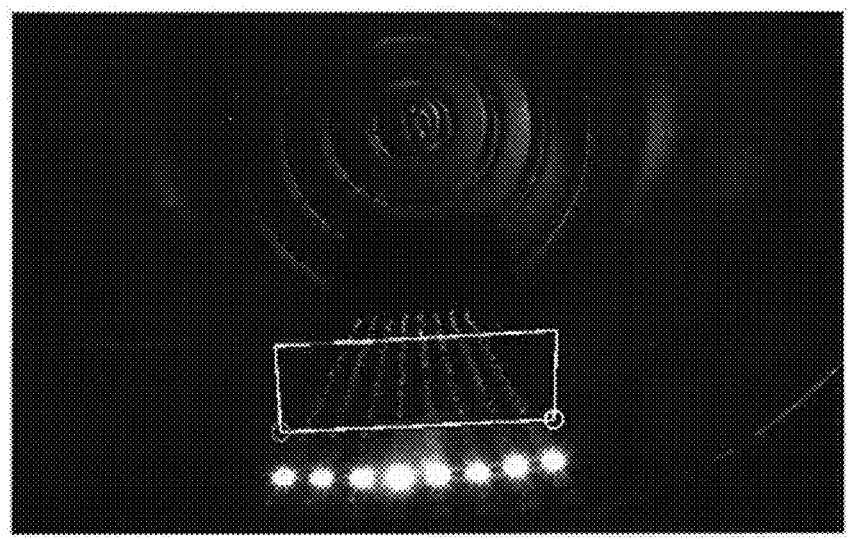

In the above equation, implicitly $h_{13}=k*z+a$, $h_{23}=k*z+b$, and $h_{33}=k*z+c$, for any plane located at z in 3D, where k is a scale parameter, and a, b, c are shifts. For simplicity z is defined at zero for the two light source column plane. A plane at different z, that is parallel to the two light source column plane geometry can be defined by simply shifting, $h_{13}$, $h_{23}$, and $h_{33}$ by equal amounts. Using the above equations, it is possible to define a photon collection region of interest (ROI) in 3D and to project the corners of the ROI to the camera coordinate system, hence incorporating the 3D perspective geometry in the photon counting calculations. The ROI should preferably include the position of a triggered light source and also be wide enough to capture forward scattered light from the light source. The ROI may e.g. encompass at least 10 times the (projected) cross section area of the light source, such as at least 100 times the cross section area of the light source. In FIG. 10, white rectangular boxes projected to the camera coordinate system show example ROIs for different light source height locations (in this case for an LED array with eight parallel columns of LEDs). The rectangle in the top image shows an ROI at far field, and the bottom image is an example for near field. The ROI is a user-determined variable, set as the volume the user wants to collect the signal from. The projective geometry calculations are then used to make sure that this volume is constant in real space, despite the projective corrections that need to be made towards what number of area the light is being collected on the actual photoreceptor of the camera (i.e., at a farther distance, the light from the real ROI volume will be collected with a smaller number of pixels on the camera, where as at closer distances, light from the same ROI volume will take up a greater number of pixels on the camera.) In other words, the ROI is a user defined variable that with the projective geometry is used to tell the camera what areas of data it should and shouldn't use. The ROI can be determined regardless of whether the light is from a single column of light sources or from a multiple column array. In the case where the scattering pattern is to be used for foam morphology assessments, it can be advantageous to define multiple ROIs for a single image.

Figure 11:
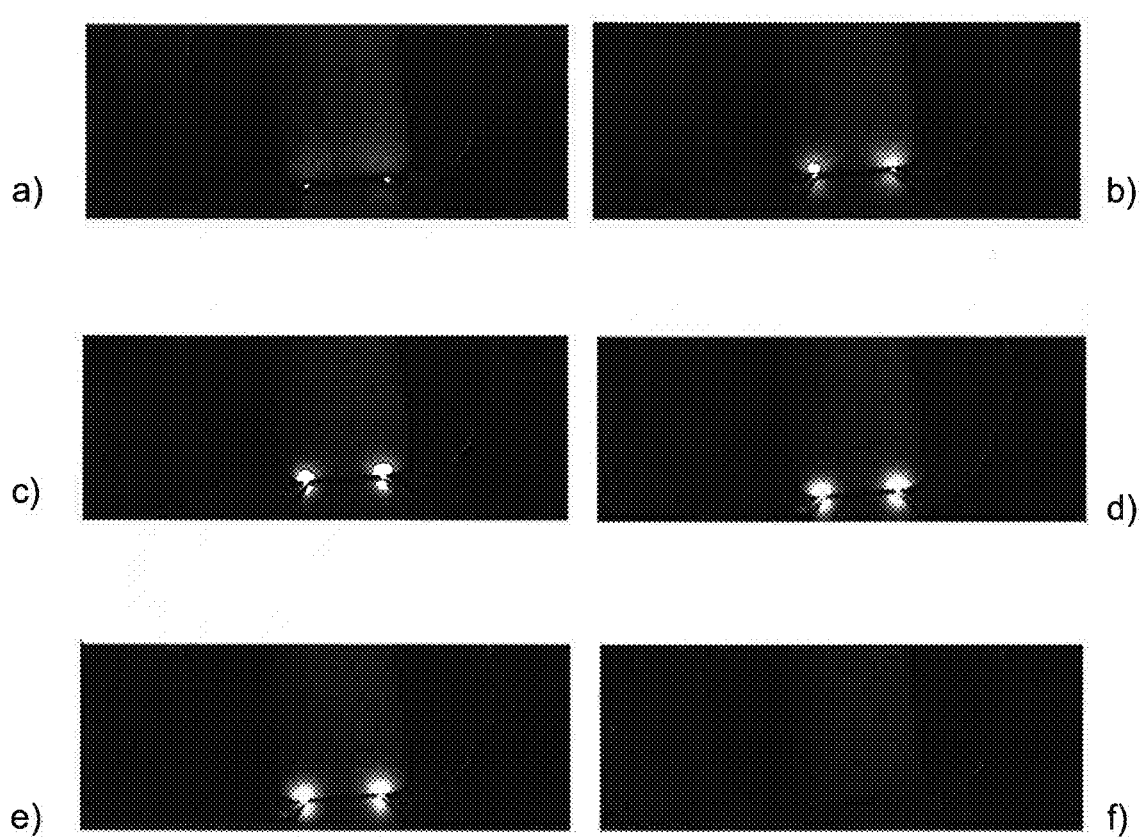
FIG. 11 shows image formation at the camera sensor at 6 sample heights. The LED number that is triggered is: a) No. 47, b) No. 50, c) No. 51, d) No. 52, e) No. 53 and f) No. 60. Number 0 refers to the first LED element closest to the camera. The number increases towards the bottom of the bioreactor. In this example the LED element at the bottom of the bioreactor is element number 78. The photon count is very low when LED elements are far from top of the foam (a, LED No. 47) or when they are inside the liquid (f, LED No. 60). When LED elements are close to top of foam surface, photon counts at the camera sensor are high due to surface reflections. In the above example these are observed at LED elements 47-51 (a-c). When LED elements are inside the foam, the photon counts at the camera sensor is mostly due to scattering (LED elements 52-53 (d-e) in the above example).

FIG. 11 shows image formation at the camera sensor at 6 sample heights (here with two parallel columns of LED light sources). The light source number that is triggered is a) No. 47, b) No. 50, c) No. 51, d) No. 52, e) No. 53 and f) No. 60. Number 0 refers to the first light source element closest to the camera. The number increases towards the bottom of the bioreactor. In this example the light source element at the bottom of the bioreactor is element number 78. The photon count is very low when the light source elements are far from the top of the foam or when they are inside the liquid. When the light source elements are close to the top of the foam surface, photon counts at the camera sensor are high due to surface reflections. In the above example these are observed at light source elements 47-51. When the light source elements are inside the foam, the photon counts at the camera sensor are mostly due to scattering (light source elements 52-53 in the above example), and are high with a decaying pattern.

Figure 12:
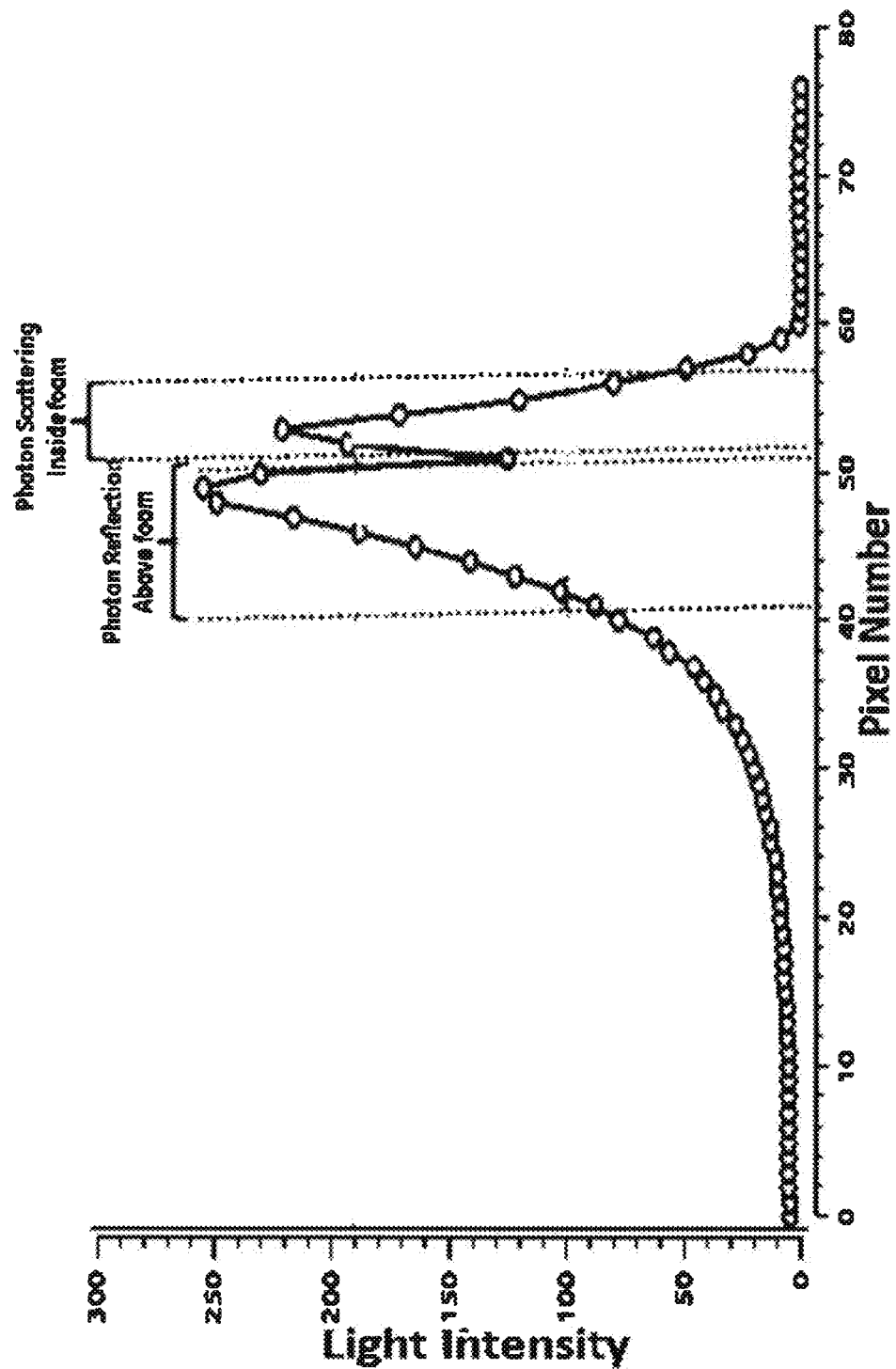
FIG. 12 shows experimental data with average photon counts within an ROI defined in real world coordinate system to compensate for geometry variations due to perspective projection from real world coordinate system to camera coordinate system. Zero indicates the first LED element, and each number in the x-axis indicates the LED number. Since LEDs are equally spaced, 7 millimeter apart, distance measurements can be easily calculated. The first peak in the distribution is due to reflections from the top of the foam, whereas the second peak is due to photon scattering inside the foam. In this example the real foam thickness is 5 cm (measured manually), and the estimated foam thickness from the photon count measurements is 4.2 cm.

FIG. 12, for a sample foam thickness, illustrates average light intensities within an ROI defined in a real world coordinate system to compensate for geometry variations due to perspective projection from the real world coordinate system to the camera coordinate system. Zero indicates the first light source element from the top, and each number in the x-axis indicates the light source number, with number 78 at the bottom of the reactor vessel. Since the light sources are equally spaced, (7 millimeter apart in this particular setting), distance measurements can be easily calculated. The first peak in the distribution is due to reflections from the top of the foam, whereas the second peak is due to photon scattering inside the foam. In this example the real foam thickness is 5 cm, and an estimated foam thickness is 4.2 cm.

Figure 13:
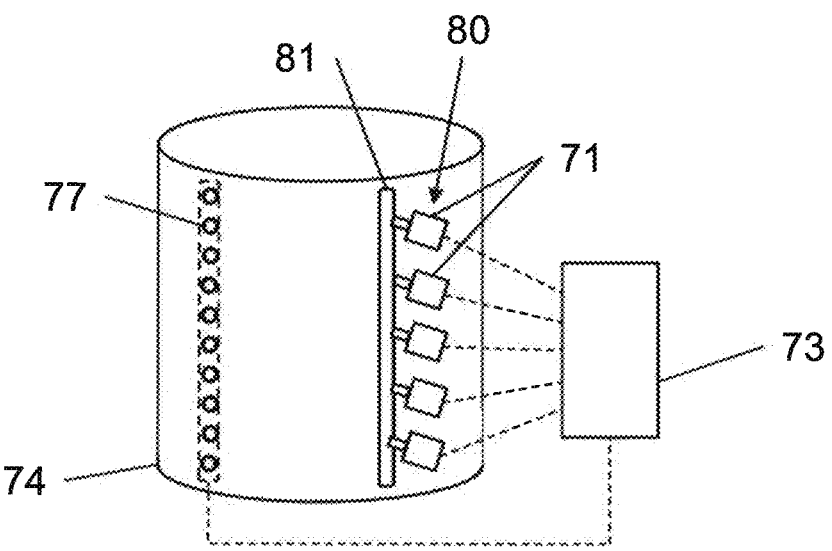
FIG. 13 shows alternative optical systems for a bioreactor with an optical opening (slit):
a) A column or array of cameras capture scattered light generated by an LED column or array. The cameras collect data through a slit (opening) on the bioreactor.
b) A moving camera controlled by a 1D motion controller collects scattered light that an LED column or array generates. The camera collects light through a slit on the bioreactor. Both in a) and b), each element on the LED column or array can be turned on sequentially, for example one LED element at a time, to measure photon counts as a function of LED height, from which foam thickness and foam height can then be calculated.
c) Instead of placing the light source in the bioreactor such as in (a), the light source can be located at the top of the bioreactor, hence eliminating any changes inside the bioreactor.
d) Similar to (c), the camera column or array can be replaced by a moving camera. The moving camera configuration eliminates multiple cameras, but adds a moving part to the system. Moving cameras are slower in collecting data, but can provide better resolution. When the data is acquired only around the foam region, hence minimizing the limits of moving range, data collection can be significantly speeded up.
Figure 13:
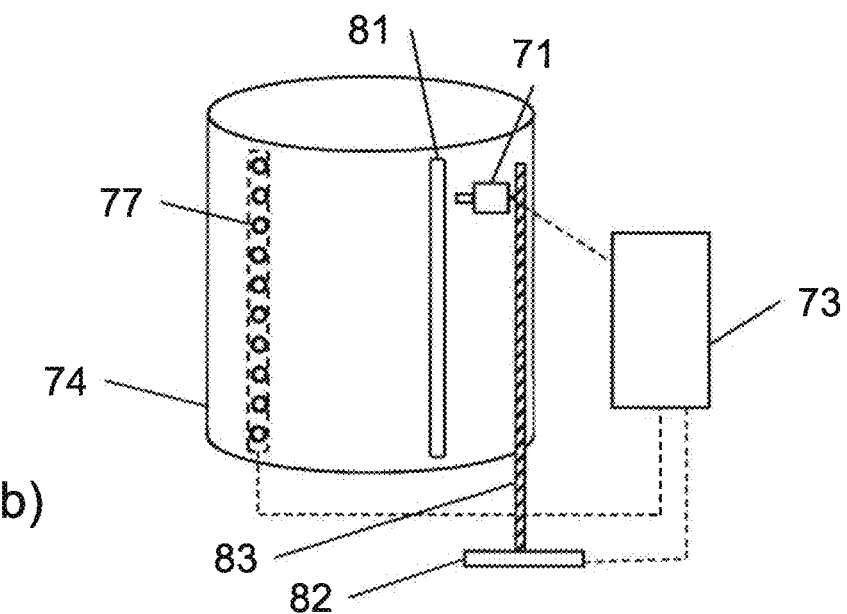
Figure 13:
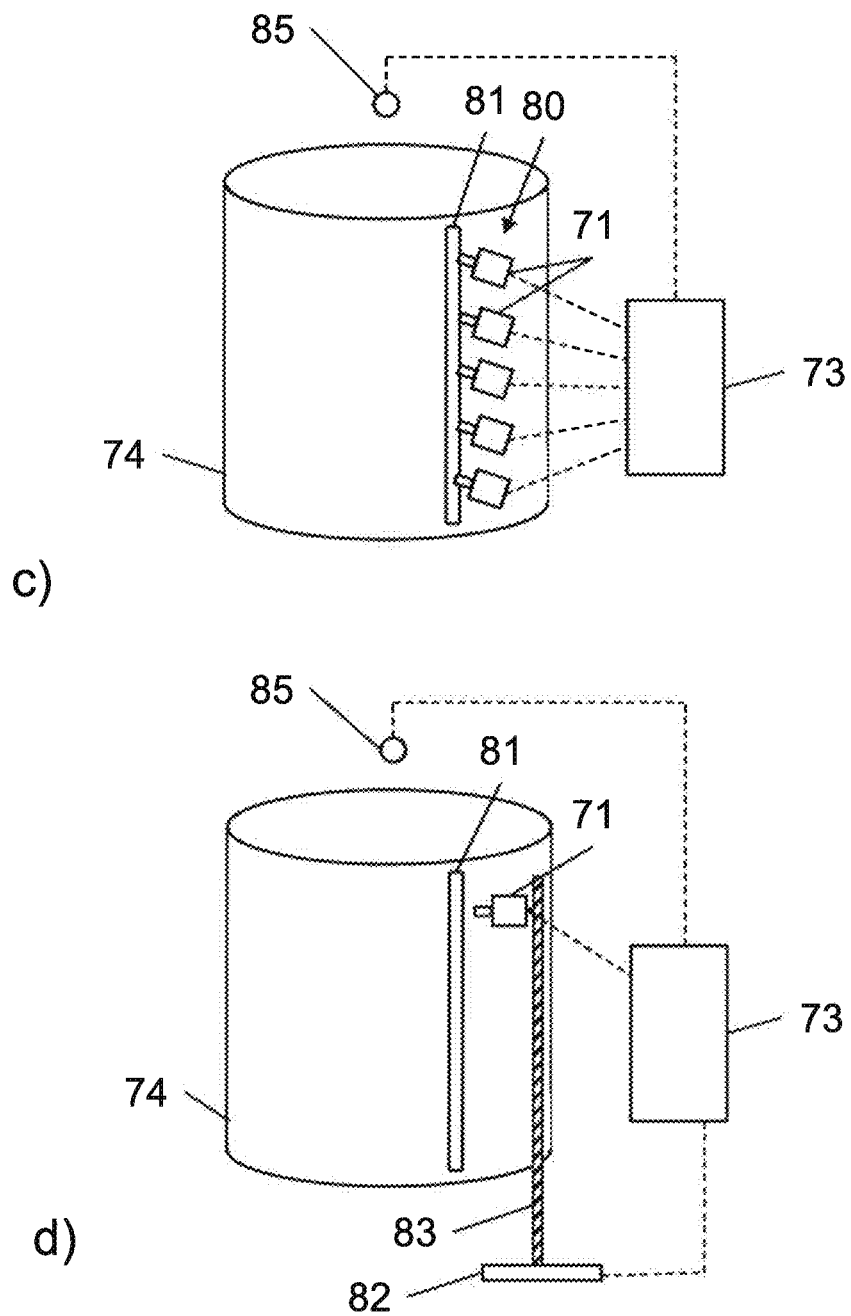

FIGS. 9-12 show one type of optical system that can be used to measure foam thickness and foam height in bioreactors. In the presence of an optical opening on the bioreactor (for example a slit window), alternative optical systems can be designed. FIG. 13 shows four alternative optical systems. In FIG. 13a, a column 80 of cameras 71 capture scattered light generated by a light source column 77 inside the vessel 74 or between an inner wall of the vessel and a transparent plastic bag inserted in the vessel. The cameras collect data through a slit (opening) 81 on the bioreactor 74. In FIG. 13b a vertically moving camera 71 controlled by a 1D motion controller 82, e.g. via a linear motor or a rotating threaded rod 83, collects scattered light generated by a light source column 77. The camera collects light through a slit on the bioreactor. Both in FIGS. 13a&b, each light source element on the light source column can be turned on sequentially, for example one light source element at a time, to measure photon counts as a function of light source height, from which foam thickness and foam height can then be calculated. FIG. 13c shows an alternative light configuration where the light source 85 is located at the top of the bioreactor, hence eliminating any changes inside the bioreactor. FIG. 13d shows similar to FIG. 13c, the camera column can be replaced by a vertically moving camera 71. The moving camera configuration eliminates multiple cameras, but adds a moving part to the system. Moving cameras are slower in collecting data, but can provide better resolution. When the data is acquired only around the foam region, hence minimizing the limits of moving range, data collection can be significantly speeded up.

In general terms, the optical systems disclosed all have at least one light source and at least one light detector, where the light source(s) produce light that is scattered and/or reflected by a foam layer to be detected by the light detector(s). For accurate determination of the foam level, the system must be capable of spatially resolved detection of the foam. This means that either the light detector(s) or the light source(s), or both, should provide spatial resolution.

The following typical cases can be outlined:

1) One or more columns of light sources where all light sources produce light (or one or more light sources extending in a vertical direction, e.g. one or more fluorescent tubes) and a camera is used to see which light sources (or which parts of the extended light source) are visible (FIGS. 1-6). Here, the camera (which can be seen as an array of light detectors with a lens system focusing an image on the array plane) provides the spatial resolution.

2) One or more columns with individually addressable light sources and a non-spatially resolved light detector (e.g. a single light detector) to detect the amount of light from an individual triggered light source (not shown). In this case, the column with the individually addressable light sources provides the spatial resolution.

3) One or more columns with individually addressable light sources and a spatially resolved light detector (e.g. a camera) to detect the amount of light from an individual triggered light source (FIGS. 9-12). In this case, both the column with the individually addressable light sources and the spatially resolved detector provides the spatial resolution.

4) One or more columns of light sources where all light sources produce light (or one or more light sources extending in a vertical direction, e.g. a fluorescent tube), or a single top-mounted light source, and a vertically moving light detector (FIGS. 13b, 13d), or a column of light detectors (FIGS. 13a, 13c). The variation in light intensity detected at different vertical positions of the light detector(s) then produces the spatial resolution. If the light detector is a camera, the spatial resolution is further improved.

5) One or more columns with individually addressable light sources and one or more columns of light detectors (FIG. 13a). Here, both the light source column(s) and the light detector column(s) provide spatial resolution.

6) A floating light source and a camera (FIGS. 7-8). Here the camera provides the spatial resolution.

7) A floating light detector and a plurality of individually addressable light sources (not shown). Here the addressable light sources can provide the spatial resolution.

Figure 14:
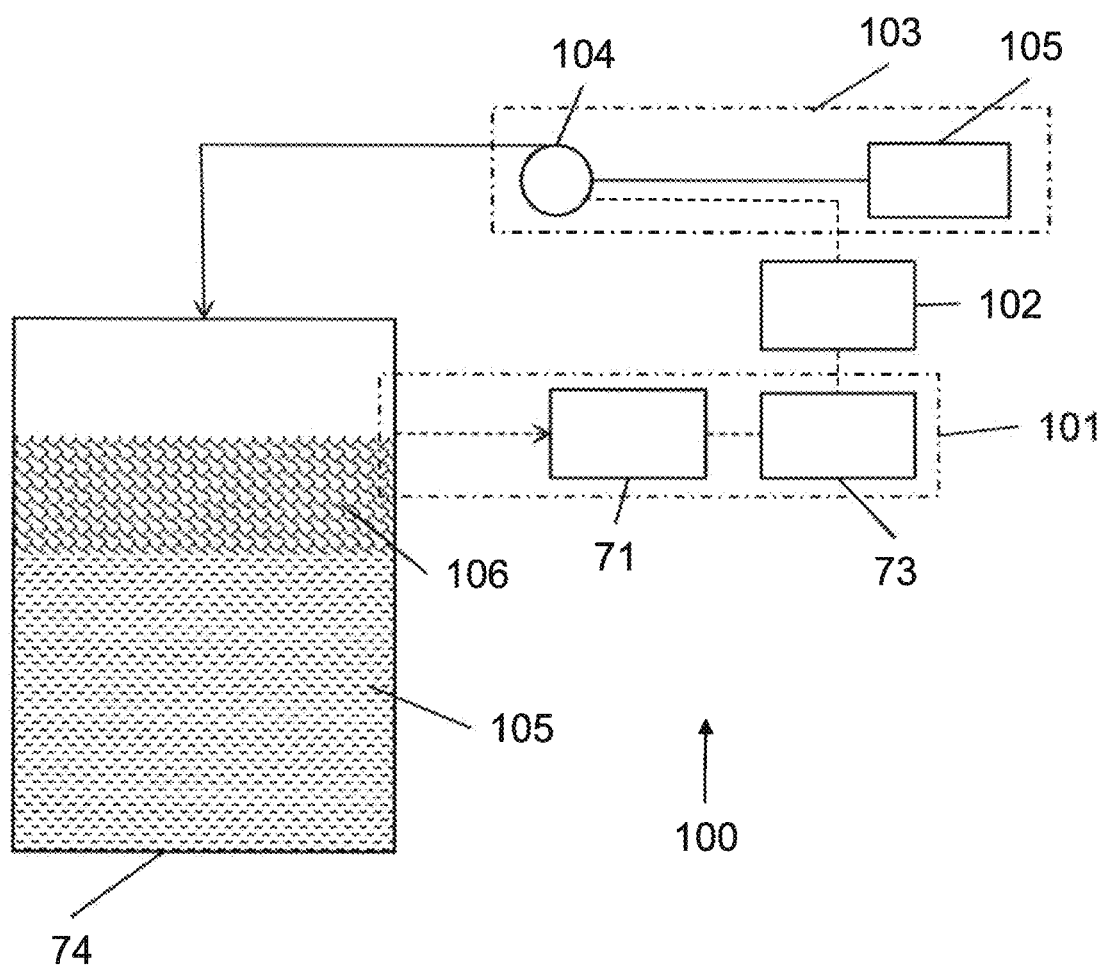
FIG. 14 shows a real world closed loop optical foam detection and de-foaming setup.

An overall workflow for a de-foaming closed loop system 100 is shown in FIG. 14, with a reactor vessel 74 containing a liquid 105 and a foam layer 106 on top of the liquid.

The de-foaming closed loop system 100 comprises a foam thickness measurement system 101, a control system 102 and a pump system 103. The control system 102 that controls the pump 104 to dispense appropriate amount of de-foaming agent from a reservoir 105 to the bioreactor 74 is based on information it receives from the thickness measurement system. LED lights or other light sources are mounted on a column or array support that is placed between the bioreactor bag and the bioreactor support vessel as discussed above. The thickness measurement system comprises a vision system, with one or more light detectors/cameras 71 and a computer 73 as discussed above, that measures the foam thickness and communicates with the control system 102, which may optionally be integrated with computer 73. The control system commands the pump to dispense appropriate amounts of de-foaming agent. The rate of foam thickness decreases as the de-foaming agent dosage completely releases in the cell culture media.

The foam thickness measurement system also provides the rate of change in the foam thickness. Right after the thickness of the foam is measured, de-foaming agent is dispensed to the cell culture fluid in the bioreactor tank/bag. Real temporal data is captured when the de-foaming agent is added to the bioreactor. We have measured how the thickness of foam changes as the de-foaming agent was added to the bioreactor.

The light sources and the camera image captures can be synchronized so that when the light source turns on, an image of the foam is acquired as well. The intensity of the scattered light varies due to the backward and forward light scattering and how deep the light source is in the foam or below the foam (for example in the fluid) or how high it is above the foam. While the defoaming agent is added, the sampling rate of the foam measurement system can be changed, since the foam thickness changes much more drastically as soon as defoaming agent is added.

The light sources (e.g. LED lights) are in an addressable column or array and are controlled individually for their color and their light intensity. The specific light source height and location is known and when it turns on an image is captured at the same time. The images are analyzed for their light intensity and foam density and morphology. Each image provides unique information based on the forward and backward scattered light behavior. By knowing the height of the light source and the amount of the light intensity captured, the foam thickness can be determined. When the foam thickness goes above certain threshold, the control system sends a signal to turn on the de-foaming agent pump valve to dispense the appropriate volume in the bioreactor tank. The graph in FIG. 17 shows that the de-foaming rate correlates with foam thickness in a closed loop de-foaming system. Also, with this system an operator can predict accurately how much de-foaming agent is required to lower the foam thickness at a desired time interval.

Current practice to control maximum foam height is to monitor the foam thickness in certain time intervals, and when foam thickness reaches above a certain threshold, the operator adds an approximate amount of defoaming agent. If the defoaming agent is not sufficient to defoam all the foam, more is added. It is very likely that the operator overestimates the amount of defoaming agent in the first trial. Or they may end up using more defoaming agent than is needed after a few trials and errors. It is not possible for a human operator to check the rate of change—in other words how quickly the defoaming agent reacts with the foam. Since different biological cell cultures may result in different foam morphology and size distribution, it is also not very precise to come up with the very first estimate for defoaming agent. With the methods of the invention it is possible to, when a foam layer is detected, add a small amount of de-foaming agent, determine the rate of foam height decrease and from this rate adjust the de-foaming agent addition rate. The de-foaming agent addition rate can e.g. be controlled by the first derivative of the foam layer thickness vs time. This allows efficient foam control with a minimal amount of de-foaming agent. If the foam layer thickness detection is impaired by residual foam adhering to the reactor walls, the timing in the control loop may be delayed to take into account that foam on the reactor walls may take longer time to collapse than foam in the center of the reactor.

The invention can precisely measure the foam thickness as well as a rate of change in the foam thickness, hence feeding this information to a controller to accurately predict the amount of defoaming agent needed. As the defoaming agent is pumped, in real time it updates the estimate of needed defoaming agent based on rate of change in the foam thickness. Thus, the system prevents overusing defoaming agents, and hence increases the quality of the cell culture and viability due to decreased side-effects of defoaming agents.

The scope of the present disclosure is defined by the following claims rather than by the detailed description of the embodiment. It shall be understood that all modifications and embodiments conceived from the meaning and scope of the claims and their equivalents are included in the scope of the present disclosure.

The invention claimed is:

1. A method, comprising the steps of:
   a) providing a reactor vessel with at least one light source which may be monitored to indicate the height level of any liquid and/or any foam inside the reactor vessel;
   b) providing at least one camera or light detector positioned to monitor said at least one light source;
   c) monitoring the intensity of light detected by the camera or light detector from said at least one light source; and
   d) from the intensity of light detected, determining a height level of a foam layer in the reactor vessel, a thickness of the foam layer and a rate of change of the thickness of the foam layer inside the reactor vessel.

2. The method of claim 1, wherein either the light detector(s) or the at least one light source, or both, are capable of providing spatial resolution.

3. The method of claim 1, wherein said at least one light detector comprises at least one camera.

4. The method of claim 1, wherein said at least one light source comprises a set of vertically spaced light sources, such as wherein light sources are arranged in a column or array along an inner wall of the reactor vessel.

5. The method of claim 4, wherein the vertically spaced light sources are arranged in a vertical line along an inner wall of the reactor vessel.

6. The method of claim 5, wherein the light sources are arranged in a staggered or oblique line along an inner wall of the reactor vessel.

7. The method of claim 1, wherein the light sources are individually addressable.

8. The method of claim 1, wherein the light sources are LEDs.

9. The method of claim 1, wherein the light sources emit visible light or near infrared radiation.

10. The method of claim 4, wherein the at least one camera or light detector collects scattered and/or reflected light from the vertically spaced light sources and wherein a computer which controls the light sources, processes data from the camera or light detector to measure the foam layer height level, the thickness of the foam layer and the rate of change of the thickness of the foam layer in the reactor vessel.

11. The method of claim 10, wherein in step c) each light source is triggered independently and said camera or light detector collects a series of images or light intensity data from triggered light sources at different heights.

12. The method of claim 11, wherein in step c) the light intensity is measured over at least one region of interest (ROI) of each image obtained from a camera, where the ROI comprises the position of a triggered light source.

13. The method of claim 12, where the ROI comprises an area of at least 10 times the cross section area of the triggered light source, such as at least 100 times the cross section area.

14. The method of claim 12, wherein in step c) the images are transformed to a coordinate system in a plane or volume comprising the triggered light sources.

15. A method, comprising the steps of;
   i) determining a height level of a foam layer in a reactor vessel, a thickness of the foam layer and a rate of change of the thickness of the foam layer;
   ii) calculating a suitable amount and/or an addition rate of an antifoam agent to add to the reactor vessel to defoam the foam layer, the amount and/or the addition rate of the antifoam agent calculated as a function of the determined height level of the foam layer, the thickness of the foam layer and the rate of change of thickness of the foam layer; and
   iii) adding said amount, optionally at said addition rate to said reactor vessel.

16. The method of claim 15, further comprising, after step iii), a repetition of step i) and, if needed, a repetition of steps ii) and iii).

17. The method of claim 16, wherein steps i)-iii) are repeated until the height level of the foam layer, the thickness of the foam layer and the rate of change of thickness of the foam layer has reached a predetermined level.

18. The method of claim 15, wherein the calculation in step ii) is performed using a stored calibration function.

19. The method of claim 1, further comprising ascertaining foam morphology information from the intensity of light detected, the foam morphology information including density of the foam layer, bubble size of bubbles in the foam layer, and a presence of particulates in the foam layer.

20. The method of claim 1, further comprising:
   predicting an amount of a defoaming agent that will lower the foam layer in the reactor vessel as a function of the height level of the foam layer, the thickness of the foam layer and the rate of change of the thickness of the foam layer;
   applying the predicted amount of defoaming agent to the reactor vessel;
   monitoring the rate of change of the thickness of the foam layer in response to applying the predicted amount of the defoaming agent to the reactor vessel; and
   changing the amount of the defoaming agent that is applied to the reactor vessel in accordance with the monitored rate of change of the thickness of the foam layer.

21. The method of claim 1, wherein the providing of the at least one camera or light detector comprises placing a first camera or light detector about a top region of the reactor vessel and a second camera or light detector about a side wall of the reactor vessel.

\* \* \* \* \*